United States Patent
Grez et al.

(10) Patent No.: US 7,067,945 B2
(45) Date of Patent: Jun. 27, 2006

(54) APPARATUS FOR CONVERTING SIDE-TO-SIDE DRIVING MOTION TO ROTATIONAL MOTION WITH A SPRING ASSEMBLY AND SYSTEM FOR TUNING THE SPRING ASSEMBLY

(75) Inventors: Joseph W. Grez, North Bend, WA (US); Jeffrey R. Gueble, Bainbridge Island, WA (US); Jerry C. Wood, Fall City, WA (US); Devin M. Nelson, Seattle, WA (US); Kevin A. Miller, Bellevue, WA (US); Craig D. Hanela, North Bend, WA (US); Bruce E. Taber, Bothell, WA (US); Richard K. Taylor, Fall City, WA (US); William Bryant, North Bend, WA (US); Scott E. Hall, Issaquah, WA (US); Andreas Loibnegger, Bellevue, WA (US); Piet C. J. van Rens, Le Asten (NL); Kurt Sadek, Klagenfurt (AT); Paulus L. W. M. Barten, Horn (NL); D. I. Stephan Leitner, Kappel am Krappfeld (AT)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/137,962

(22) Filed: May 3, 2002

(65) Prior Publication Data

US 2003/0204924 A1  Nov. 6, 2003

(51) Int. Cl.
*H02K 7/14* (2006.01)
*A46B 13/00* (2006.01)

(52) U.S. Cl. .............. 310/50; 310/21; 310/17; 310/12; 310/47; 15/22.1

(58) Field of Classification Search .............. 310/50, 310/20, 37, 36, 17, 21, 29, 32, 119, 12; 74/89; 15/22.1, 22

See application file for complete search history.

(56) References Cited

U.S. PATENT DOCUMENTS 3,538,359 A * 11/1970 Barowski .................... 310/29

(Continued)

FOREIGN PATENT DOCUMENTS

JP        09187319 A  *  7/1997

*Primary Examiner*—Darren Schuberg
*Assistant Examiner*—Yahveh Comas
(74) *Attorney, Agent, or Firm*—Adam L. Stroud (57) ABSTRACT

The apparatus for converting side-to-side to rotational motion for a workpiece includes a spring assembly with a movable base mounting element which is driven in a slightly arcuate reciprocal side-to-side motion and a fixed mounting element spaced apart from the base element and mounted in the appliance so that it does not rotate or move in operation of the apparatus. A spring member, such as two planar leaf springs positioned at an angle to each other, is mounted between the movable base element and the fixed mounting element. A drive shaft member extends from the movable base element through the fixed mounting element and beyond. A workpiece such as a brushhead is mounted on the distal end of the drive shaft. The spring member is configured so that it is substantially less resistant to twisting action than bending action, such that the side-to-side motion of the base element results in rotation of the workpiece.

A method for tuning resonant spring assembly systems used in appliances such as power toothbrushes, particularly leaf spring systems, includes the step of measuring the frequency-dependent amplitude of the appliance workpiece, and then removing a portion of the spring member so as to decrease its spring rate sufficiently that the resonant frequency of the spring member closely approximates the drive frequency of the appliance.

27 Claims, 5 Drawing Sheets

U.S. PATENT DOCUMENTS

| | | | |
|---|---|---|---|
| 5,189,751 A | * 3/1993 | Giuliani et al. | 310/36 |
| 5,263,218 A | * 11/1993 | Giuliani et al. | 310/36 |
| 5,378,153 A | * 1/1995 | Giuliani et al. | 15/22.1 |
| 5,613,259 A | * 3/1997 | Craft et al. | 310/50 |
| 5,955,799 A | * 9/1999 | Amaya et al. | 310/36 |
| 6,189,693 B1 | * 2/2001 | Blaustein et al. | 15/22.1 |
| 6,779,215 B1 | * 8/2004 | Hartman et al. | 15/22.1 |
| 6,895,624 B1 | * 5/2005 | Fischer et al. | 15/22.1 |

* cited by examiner

APPARATUS FOR CONVERTING SIDE-TO-SIDE DRIVING MOTION TO ROTATIONAL MOTION WITH A SPRING ASSEMBLY AND SYSTEM FOR TUNING THE SPRING ASSEMBLY

TECHNICAL FIELD

This invention relates generally to small appliances, such as, for instance, toothbrushes, and more specifically concerns a spring structure for converting a side-to-side driving action into a rotary workpiece action. The invention also concerns a method for tuning the spring structure to a selected natural resonant frequency or amplitude during manufacture.

BACKGROUND OF THE INVENTION

Small appliances have various workpiece motions. In some cases, the drive motion is the same as the workpiece motion; in other cases, it is desirable to convert a particular drive motion into a different workpiece motion, such as a side-to-side drive motion to a rotary motion. The magnetic driver shown in U.S. Pat. No. 5,189,751 moves one end of an elongated pivoted arm to which is attached a toothbrush element, in a side-to-side (back and forth), slightly arcuate manner. The workpiece vibrates in a particular manner accordingly. While that workpiece motion does provide good results, it may be desirable, for various reasons, to have the workpiece rotate through a selected arc (rotational motion), while retaining the side-to-side driving action. This would require, however, a motion conversion assembly, from side-to-side to rotational.

Apparatus for converting a side-by-side driving action, such as produced by the electromagnetic driver of the '751 patent, to a workpiece rotary action are known. Some devices involve linkage-type arrangements. However, such linkage arrangements frequently have undesirable backlash action, which can cause damping, vibration and noise. Pivot assemblies are also used, in combination with a spring element. Torsion springs can be used, but they are usually made from coil-type springs, which typically do not combine the required radial stiffness with an acceptably low torsion spring rate. Most of these known devices require various bearing structures, which are often complex, noisy and unreliable. Bearings also have their own backlash conditions.

Further, in another aspect of the present invention, spring elements are often used as part of a driving assembly in a resonant system, such as the spring assembly of the present invention. These spring assemblies usually require either tuning in some fashion or very close manufacturing tolerances, so that the resonant frequency of the spring assembly is acceptably close to the operating or drive frequency of the device, to maintain the efficiency of the resonant system.

With respect to the motion conversion assembly aspect of the present invention, it is desirable that the conversion assembly be efficient, reliable and inexpensive to manufacture. With respect to the spring assembly tuning, it is desirable that the tuning be accomplished with a simple method which can be carried out during manufacture of the assembly so that the manufacturing tolerances of the appliance can be increased (greater tolerances), thereby decreasing the cost of manufacture of the appliance, as well as substantially reducing the number of appliances rejected during manufacture.

SUMMARY OF THE INVENTION

Accordingly, one aspect of the present invention is an apparatus and corresponding method of converting side-to-side drive motion to rotational motion for a workpiece portion of an appliance, comprising: a movable base mounting element, capable of being driven in a translational reciprocal motion; a fixed position mounting element spaced apart from the base element, the fixed mounting element being held so that it does not move during operation of the apparatus; a spring member connected to the base element and to the fixed mounting element; and a drive shaft member connected to the base element and rotatable relative to the fixed mounting element, the drive shaft having a workpiece mounted thereto, wherein the spring member is so configured and arranged that it is substantially less resistant to twisting action than to bending action, the twisting action producing workpiece rotation at a preselected frequency.

Another aspect of the present invention is a method for tuning a spring member used in a resonant driving system for an appliance which includes a workpiece and which has a driving frequency, comprising the steps of: measuring the frequency dependent amplitude of the workpiece which vibrates by action of the spring member, wherein the measured frequency is either above or below a driving frequency of the appliance; and changing the spring rate of the member, and hence its resonant frequency, sufficiently that the resonant frequency of the spring member closely approximates the driving frequency of the appliance.

BEST MODE FOR CARRYING OUT THE INVENTION

Figure 1:
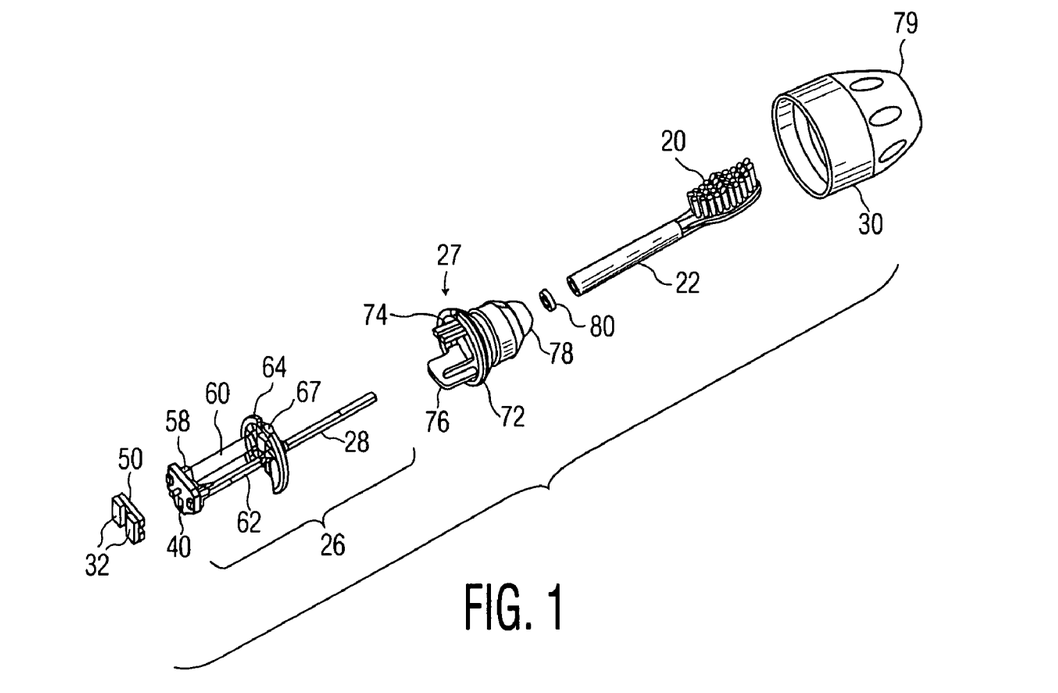
FIGS. 1 and 1A are exploded views of the motion conversion assembly of the present invention shown in the context of a power toothbrush.
Figure 1A:
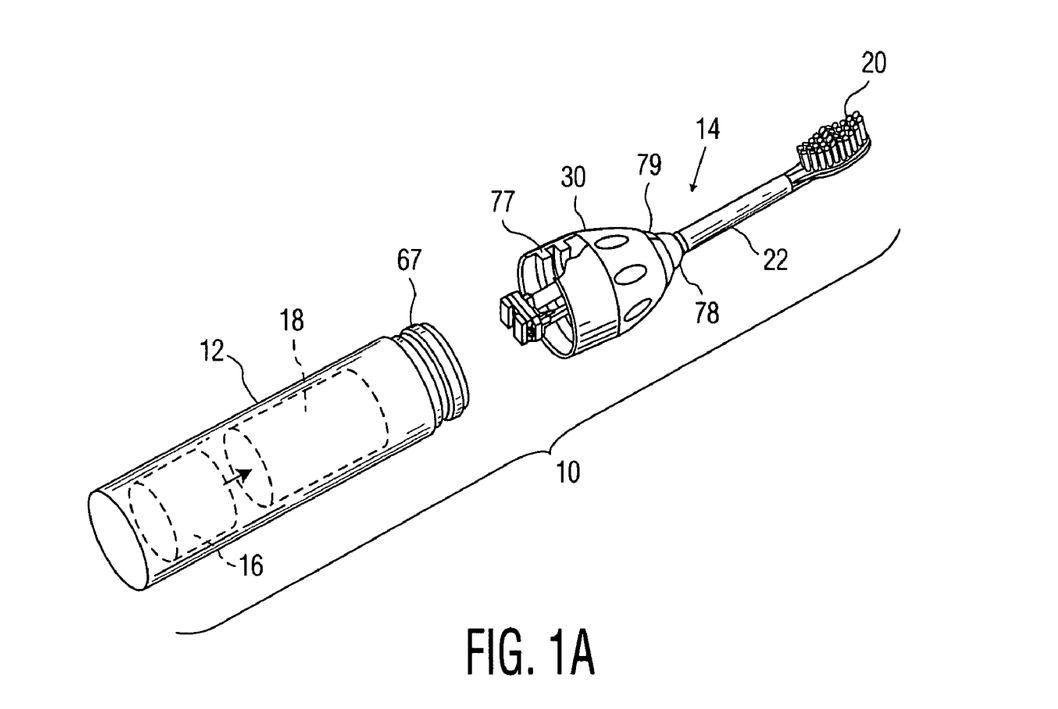

FIGS. 1 and 1A show a power toothbrush 10 which includes a handle portion 12 and a head portion 14. The handle portion includes a power source, such as a rechargeable battery 16, and a drive assembly, shown generally at 18. The head portion 14 includes a workpiece element, e.g. a brushhead 20, which comprises a plurality of bristles arranged in a selected pattern, a brushhead arm 22 on which brushhead 10 is mounted, a motion conversion assembly, shown generally at 26, and a mounting assembly 27 for the motion conversion assembly.

The motion conversion assembly 26 in the embodiment shown converts a linear action to rotation of a drive shaft 28 which extends into and joins with brushhead arm 22 for rotation thereof and rotation of brushhead 20. Head portion 14 also includes a nut element 30, which connects head portion 14 to handle portion 12 and to which the mounting assembly 27 is fixedly secured.

Figure 2:
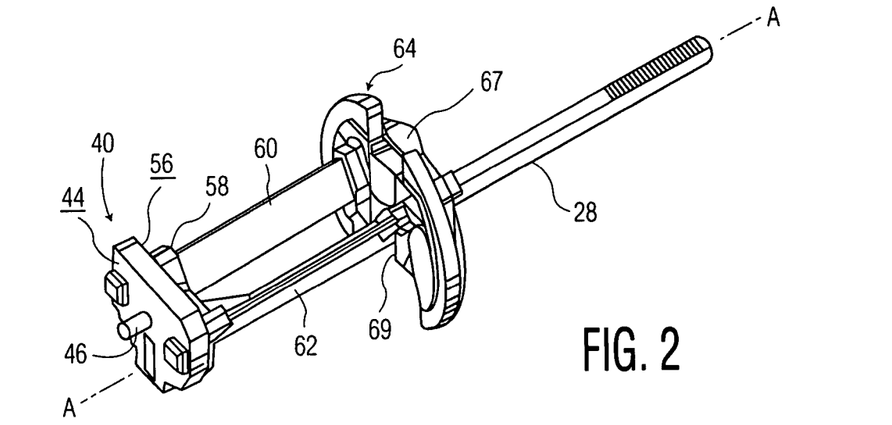
FIG. 2 is a perspective view of the motion conversion assembly portion of FIG. 1.

In the appliance shown, the driving assembly 18 is an electromagnet, which produces a side-to-side force and cooperates in operation with two permanent magnets 32 mounted to a movable end piece 40 at the rear end of the motion conversion assembly 26 to move end piece 40 in a side-to-side slightly arcuate, translational manner. "Side-to-side" herein refers to a straight side-to-side motion or a side-to-side path which is slightly arcuate. The motion conversion assembly 26 converts the drive action of the drive assembly via a leaf spring arrangement into a twisting or rotational action of drive shaft 28, which in turn rotates brushhead arm 22 and brushhead 20 about the longitudinal axis A—A of drive shaft 28 (FIG. 2). In the embodiment shown, the included angle (arc) of rotation of the brushhead is approximately 11°, although this angle can be varied and is not an essential part of the present invention.

The motion conversion assembly 26 is shown in more detail in FIG. 2. It includes movable end piece 40, which in the embodiment shown is made from a plastic material and is approximately 0.6 inches long, approximately 0.6 inches wide at its widest dimension, and approximately 0.1 inches thick. Extending from the rear face 44 of end piece 40 is a small, centrally located mounting stub 46. Mounted on stub 46 is a permanent magnet assembly, which in the embodiment shown comprises a metal mounting plate 50 (FIG. 1) and two spaced rectangular permanent magnets 32—32. Permanent magnets 32—32 interact with electromagnet 18 in handle 12 such that the movable end piece 40 moves from side-to-side in a slightly arcuate path. This action is explained in more detail in the '751 patent, the contents of which are hereby incorporated herein by reference. However, it should be understood that the side-to-side drive action by the drive assembly 18 is only one such arrangement. Many other side-to-side drivers are known and can be used with the conversion assembly of the present invention.

On the opposing face 56 of movable end piece 40 is a mounting piece 58 which is either integral with end piece 40 or is securely attached thereto. Extending forwardly from mounting piece 58 are two elongated leaf springs 60 and 62. In the embodiment shown, each leaf spring 60, 62 is approximately 1 inch long, 0.2 inches wide and approximately 0.02 inches thick. Leaf springs 60, 62 in the embodiment shown are made from metal. However, they could be made from other materials, such as plastic.

The two leaf springs 60, 62 in the embodiment shown are positioned at an angle of 70° relative to each other. The two leaf springs extend between and are fixedly mounted to both movable end piece 40 and fixed end piece 64. Fixed end piece 64 is generally circular, approximately 0.1 inches thick, and in the embodiment shown is made from plastic. It has two opposed notch openings 67, 69 at the top and bottom portions thereof.

Extending from mounting piece 58 approximately at what would be the intersection of the two leaf springs 60 and 62, if the leaf springs were so extended, is the elongated drive shaft 28. The planes of the two springs 60 and 62 intersect at the center of rotation of the motion conversion assembly, where the drive shaft is located. In the embodiment shown, drive shaft 28 is metal and is rectangular in cross-section. The drive shaft 28, however, could have other configurations. In operation, the leaf springs twist and also bend somewhat as well, producing a rotation of the drive shaft. The relative position and dimensions of the springs can be optimized to reduce stress in each spring independently.

Drive shaft 28 in the embodiment shown extends through notched opening 69 in the fixed end piece 64, so that it is free to rotate relative to fixed end piece 64. Drive shaft 28 extends to and is joined to brushhead arm 22, so that rotation of drive shaft 28 produced by the action of the motion conversion assembly produces a rotation of brushhead arm 22 and brushhead 20 mounted at the distal end thereof.

The fixed end piece 64 is secured by mounting assembly 27 SO that it does not rotate relative thereto. The mounting assembly 27 includes as a portion thereof a ring of plastic material 72, with two opposing flanges 74 and 76 which extend rearwardly therefrom. The two flanges 74 and 76 extend through the notched openings 67, 69 in the fixed end piece 64. The two flanges 74 and 76 are configured to mate with corresponding receiving portions (not shown) in handle 12 of the toothbrush to produce a secure mating connection between the mounting assembly 27 (and head portion 14) and handle 12. When flanges 74 and 76 of the mounting assembly 27 are properly positioned in the receiving portions of handle 12 and nut 30 is in place, as described below, the mounting assembly 27 and, hence, the fixed end piece 64 are held firmly from, i.e. prevented from, any rotational action. The distal ends of the two leaf springs 60 and 62 are fixedly mounted in end piece 64 and also hence prevented from moving.

Fitting over the mounting assembly 27 and the motion conversion assembly 26 is connecting nut element 30. The connecting nut element has threads 77 on its internal surface so that it can be screwed onto an external threaded portion 67 of the handle 12. The nut 30 clamps flanges 74 and 76 to the handle, with fixed end piece 64 being held in place by flanges 74 and 76. At the upper edge 79 of nut 30 is a flexible connecting member 78, which in the embodiment shown is made from an elastomeric material. The lower edge of connecting member 78 fits flush with upper edge 79 of nut 30. Member 78 extends to a seal element 77, which provides a fluid seal between brushhead arm 22 and the upper end of connecting member 78.

In operation, the side-to-side drive produced by the electromagnetic driver 18 in the handle (or any other side-to-side driver) produces a slightly arcuate action of movable end piece 40, resulting in a rotation of the brushhead 20 through a specific angle.

Figure 3:
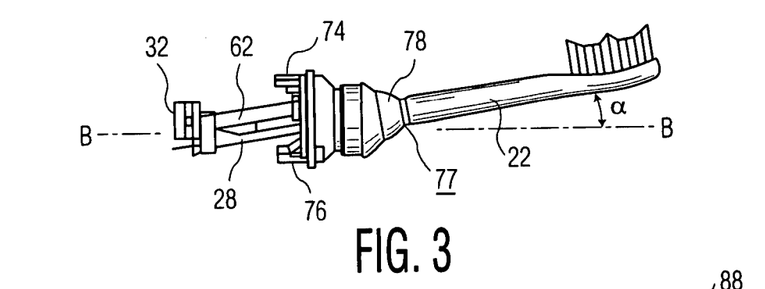
FIG. 3 is an elevational view showing the angled orientation of the drive shaft and the brush arm relative to the longitudinal axis of the toothbrush.

In the embodiment shown, the two leaf springs 60 and 62 and the drive shaft 28 are mounted in the fixed and movable end pieces such that they extend at an angle a away from the longitudinal axis B—B of the toothbrush (FIG. 3). This angle is within the range of 5–15° and preferably 10°. This angle of the brushhead arm provides an increased reach for the toothbrush into the user's mouth. This is an advantage in many instances. Further, with this arrangement, the center of rotation is on a different axis than the axis of the handle. As the center of rotation is tilted away from the longitudinal axis of the appliance, the moment of inertia of the rest of the appliance relative to the axis of rotation of the drive shaft increases rapidly, thereby reducing the vibration of the handle, since the greater the moment of inertia, the less resulting vibration in the appliance, including the handle. This is a desirable advantage for the user.

While the embodiment described includes two separate leaf springs which are at a specific angle (70°) to each other, two separate leaf springs are not necessary. The separation angle could vary within a range of 90°±40%. In addition, more than two leaf springs could be used, in a radial pattern, with the plane of the leaf springs intersecting the center of rotation of the drive shaft. The two leaf springs could be joined into a single leaf spring in a "V" or a "U" form, an open square or a rectangle. Other configurations are also possible. The drive shaft must be connected to the movable end piece portion of the system, with the springs. The drive shaft cannot be connected to any other part of the springs. This structure could be a single part. The key structural requirement is that the spring element must be configured so that it is substantially less resistant to twisting than to bending, i.e. so that the side-to-side action of the movable end piece results in a twisting of the springs and a resulting rotation of the drive shaft. The arrangement shown and described herein produces such an action. Other spring arrangements could be used, however. Further, and also importantly, the arrangement of the springs must be such that the brushhead will not only rotate, but rotate at a selected frequency.

Figures 6, 7:
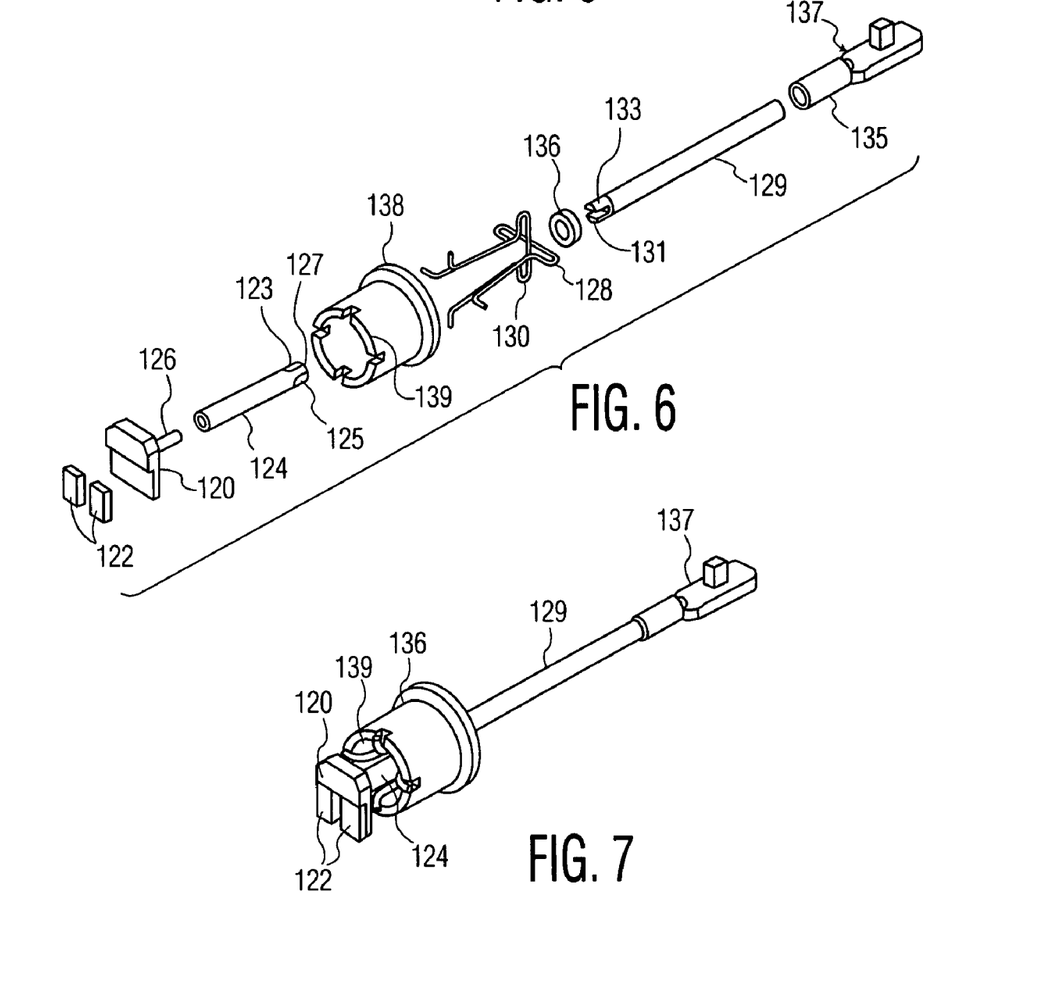
FIGS. 6–8 show one alternative embodiment to the invention of FIG. 2.
Figure 8:
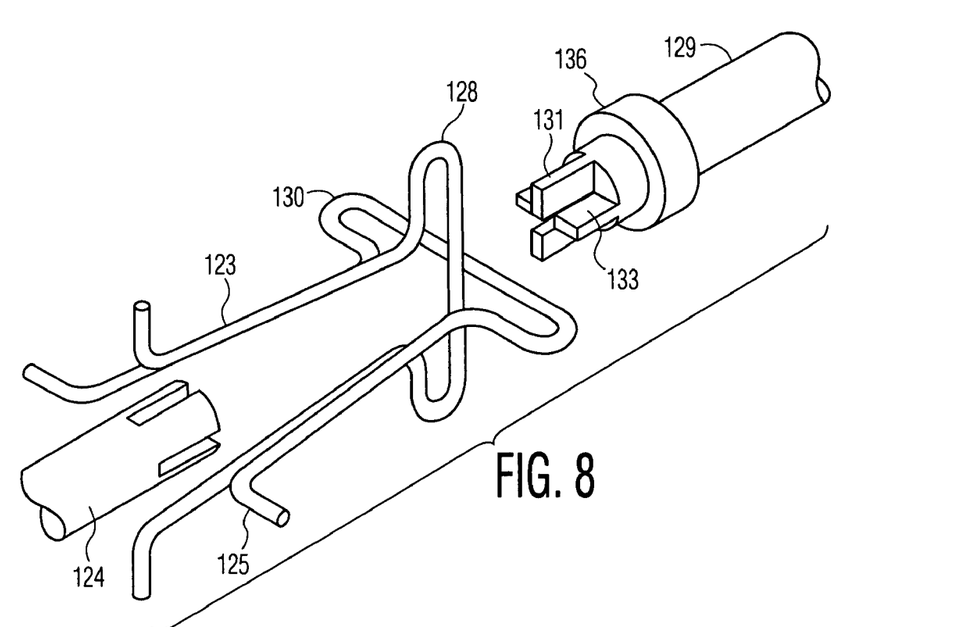

FIGS. 6, 7 and 8 show one alternative embodiment to the motion conversion assembly of FIGS. 1–3 using a particular arrangement of a wire form spring. The conversion assembly includes a back plate 120 and permanent magnets 122. An armature shaft 124 is mounted to back iron 122 on stub 126. Shaft 124 has two slots 123, 125 at 90° (orthogonal) to each other, in the distal end 127 thereof. Two wire form springs 128 and 130, also positioned at 90° (orthogonal) to each other, are inserted into the slots 123, 125. A brush shaft 129 has cross elements 131, 133 which mate with slots 123, 125, capturing the wire form springs between the respective ends of the armature shaft 124 and the brush shaft 129.

At the distal end 135 of the brush shaft is a base element 137 for a brushhead or other workpiece (not shown). A collar 136 is pressed down the brush shaft onto the armature shaft, holding the springs, the brush shaft and the armature shaft together, like a collet. The rear ends of wire form springs 128 and 130 are then captured within a spring mount 138, which is slotted 141 at its rear end 139 thereof to capture the ends of the wire form springs. The spring mount 138 is fixedly connected to the housing of the appliance. Movement of the back plate 120, caused by side-to-side force produced by the drive assembly, results in rotation of brush shaft 129.

Figures 9, 10:
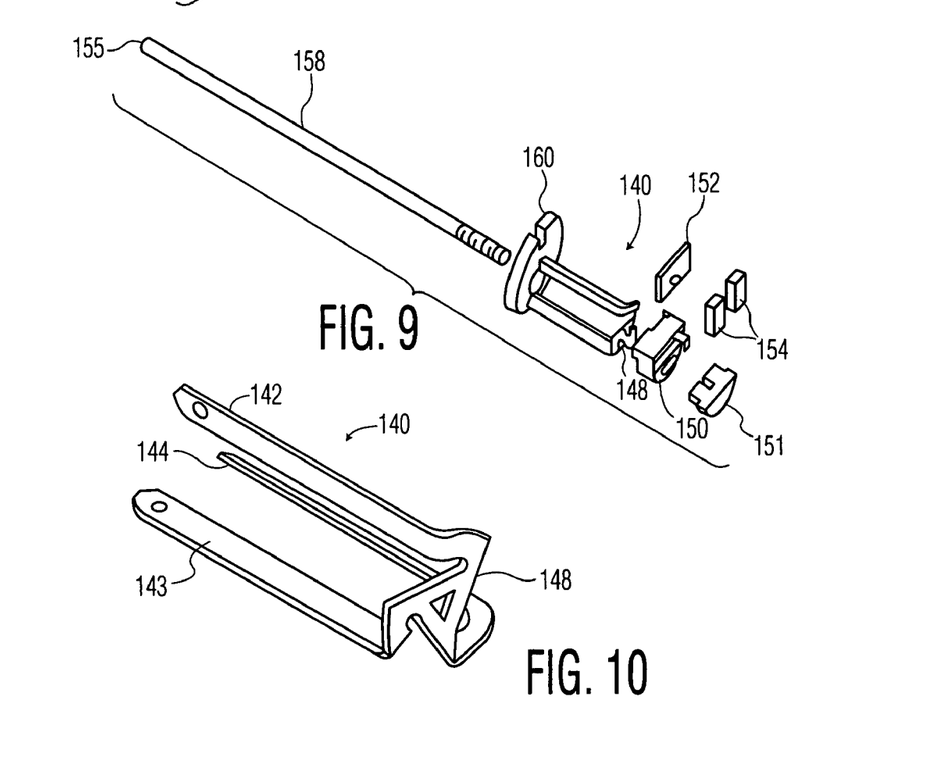
FIGS. 9–10 show another alternative embodiment of the invention of FIG. 2.

FIGS. 9 and 10 show a further embodiment. The conversion assembly includes a single-piece, multi-leaf spring 140, comprising three separate legs 142–144 joined together at one end 148. The spring 140 is mounted to a movable rear member 150, in which is positioned a tuning mass 151 from which material can be removed to tune the resonant frequency of the spring assembly. A back plate element 152 is positioned on the rear surface of the movable rear member 150, to which permanent magnets 154 are secured. A drive shaft 158 is attached to and extends from the movable member 150. To the distal end 155 of drive shaft 158 is secured a workpiece, such as a brushhead (not shown). The free ends of the spring assembly 140 are secured to a fixed mounting element 160, through which the drive shaft 158 extends. The mounting element 160 is secured to the housing of the toothbrush. Reciprocating motion of the moving member 150 results in a rotational motion of the drive shaft 158 and the workpiece.

Figure 11:
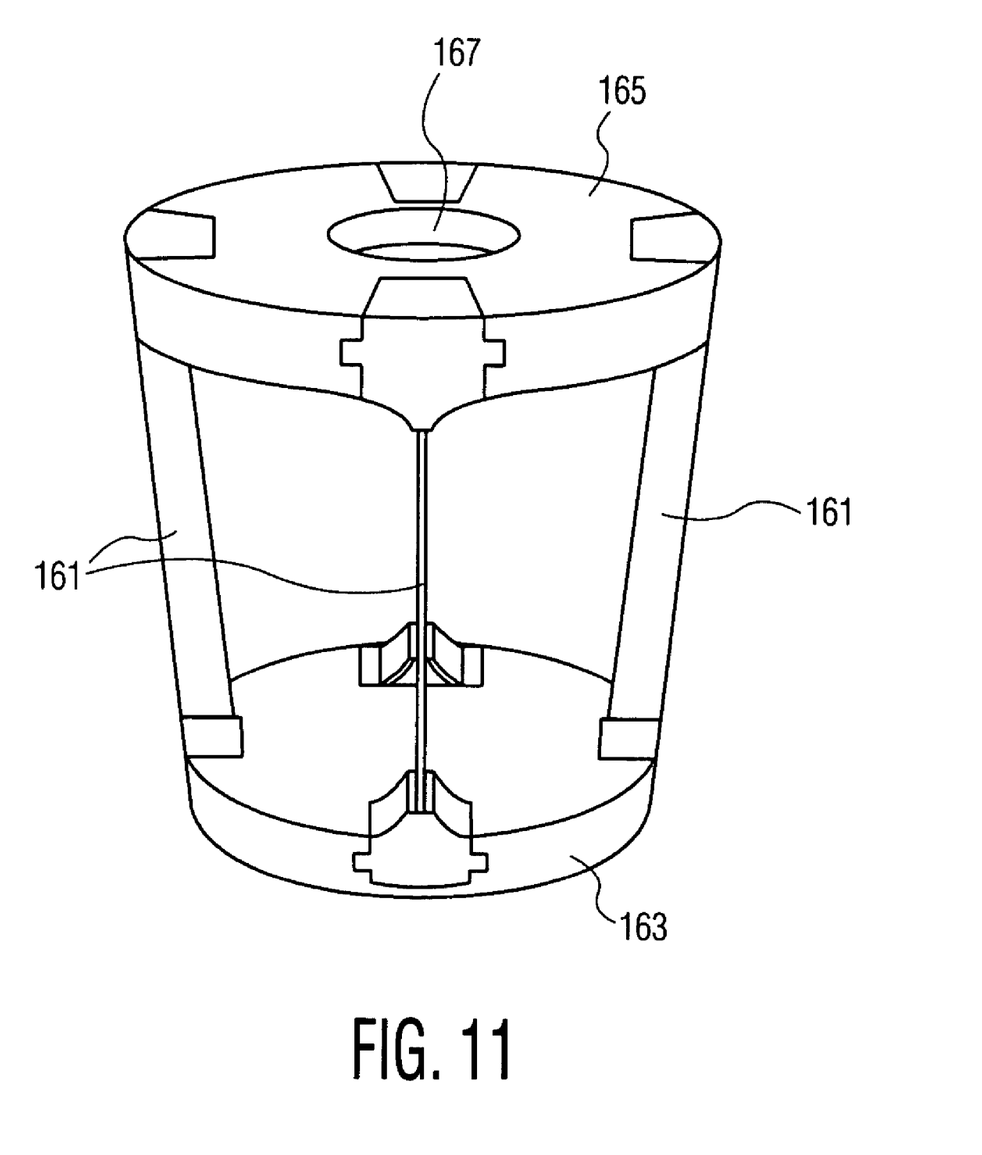
FIG. 11 shows still another alternative embodiment to the invention of FIG. 2.

Still other spring arrangements are possible, including an arrangement having a plurality of spring elements 161—161 which extend from the rear movable mounting member 163 to the fixed mounting member 165 in a somewhat basket-like arrangement. The spring elements 161—161 angle outwardly between the two mounting members. FIG. 11 shows such an arrangement with four springs. More springs could be added. The plane of each spring 161 extends through the center of rotation of the assembly. A drive shaft, (not shown) at the center of rotation of the spring assembly, will extend through opening 167 in fixed member 165 from movable member 163.

All of the above alternative configurations have the characteristic that the spring member is less resistant to twisting motion than to bending motion, producing a rotational action of the drive shaft in response to a side-to-side driving force.

Figure 4:
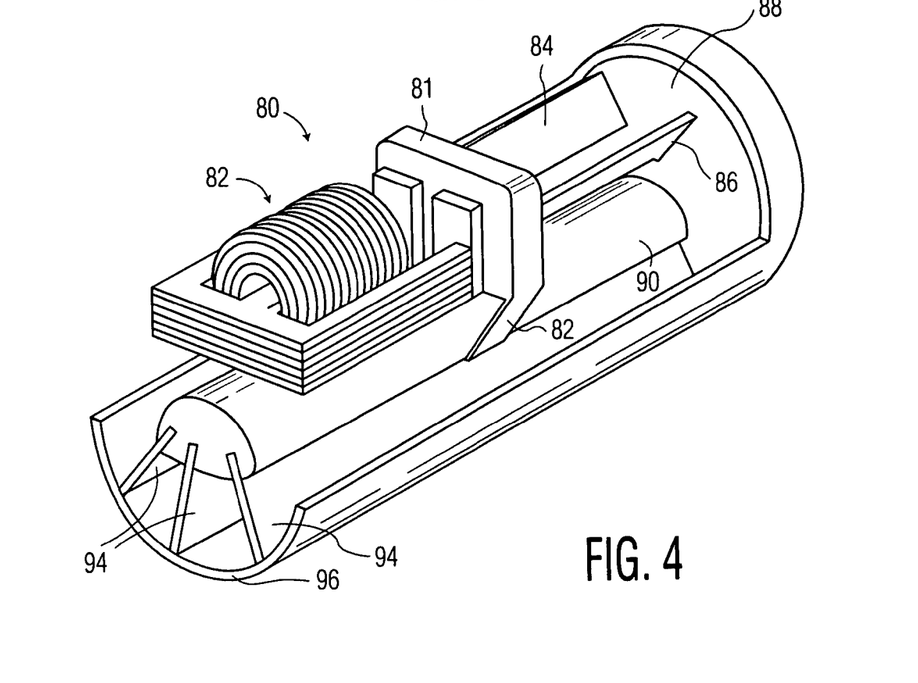
FIG. 4 shows a modified motion conversion system used for a shaving appliance.

FIG. 4 shows an alternative application for the present invention. This application, which is an electric shaver 80, also includes a movable end piece 81 with permanent magnets, driven by a magnetic driver arrangement, shown generally at 82. Extending from the movable end piece 81 are the two angled leaf springs 84 and 86, which are fixedly secured at their other ends to a fixed end piece 88. A drive shaft 90 extends rearwardly from the fixed end piece 81, parallel with the leaf springs 84, 86. The drive shaft 90 is suspended from the movable end piece 81 by support elements 82 and extends beneath the driver assembly 82.

Fixedly attached to and extending radially outwardly from drive shaft 90 are a plurality of elongated cutter blades 94, the outboard edges of which are sharpened. The outboard edges mate against a curved shaver screen element 96. In operation, the side-to-side action of the end piece 81 results in a rotation of drive shaft 90, and in turn a rotation of the cutter blades 84 through a specific angle, providing the cutting action for the shaver.

This embodiment demonstrates that the position and arrangement of the drive shaft on which the workpiece is mounted can take various configurations relative to the motion conversion spring assembly. In all cases, however, a movable end piece is driven in a side-by-side fashion, with a spring assembly extending from the movable end piece to a fixed end piece, which produces a rotary action of the drive shaft which is mounted to the movable end piece and hence a rotary action of the workpiece mounted thereon.

The present invention eliminates the need for any bearing elements or flex elements, primarily because there is little bending of the spring element. It is, however, a strong, reliable and effective structure. Furthermore, it is a resonant assembly, which can be matched to an operating (driving) frequency of the appliance. For instance, in the toothbrush embodiment, the desired operating frequency is approximately 261 Hz. The spring assembly can be arranged and constructed so that it provides rotational action at that frequency.

As indicated above, the toothbrush of FIG. 1, including the motion conversion assembly, is a "resonant" system. That is, the natural resonant frequency of the mechanical elements of the system are designed to match the operating or drive frequency of the toothbrush, which in the case of the present toothbrush is approximately 261 Hz. Such a resonant system is more efficient than a non-resonant system.

As discussed above, many approaches are known for ensuring that the resonant frequency of the spring system matches the operating frequency of the appliance. In one approach, the configuration and arrangement of the mechanical system is sufficiently accurately controlled during manufacture to provide the desired frequency match without tuning. Manufacturing tolerances must, however, be quite tight (including using more precise parts), and a substantial number of appliances are usually discarded because they do not meet the required strict manufacturing tolerances.

In another approach, various actions are taken to "tune" or modify the spring structure to produce the required frequency match with the operating frequency of the appliance.

The typical tuning process usually takes a substantial amount of time and expertise and is hence typically not cost-effective. Such tuning can be accomplished during manufacture or at times thereafter, even when the appliance is in the possession of the user.

In this aspect of the present invention, a method is disclosed for tuning a resonant spring system of a high volume product using leaf springs. The present method can be used to either increase or decrease (tuning up or tuning down) the resonant frequency of the spring assembly to match the operating frequency.

In a first step of the process, measurement of amplitude of the workpiece is made at a test frequency or vice versa. A fixed amplitude can be used with a variable frequency or a fixed frequency can be used with a variable amplitude. Both techniques can be used for tuning. Tuning the spring assembly shifts the operating point of the spring assembly on the operating characteristic curves to match the desired operating frequency or amplitude.

The point on the characteristic operating curve can be decreased (a decrease in frequency) by reducing the spring rate of the spring assembly. Alternatively, the operating point can be increased (an increase in frequency) by increasing the spring rate. While many tuning systems increase or decrease the inertia of the system by increasing or decreasing the weight of the spring system, this approach is often not very accurate and requires a fairly high amount of weight reduction or increase to produce the desired frequency matching effect. In the present invention, however, the focus is on increasing or decreasing the spring rate (instead of inertia) by changing the configuration of the spring assembly which, in the present case, are leaf springs.

Figure 5:
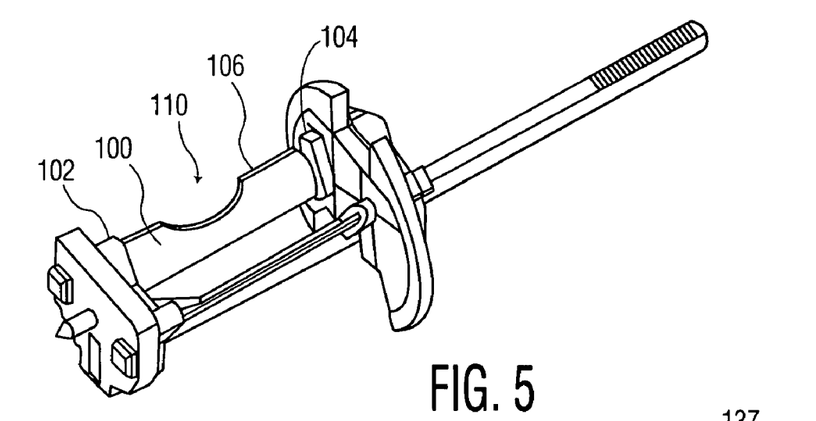
FIG. 5 shows the result of the frequency tuning method of the present invention on the motion conversion assembly of FIG. 2.

In the process to reduce the spring rate, the individual leaf springs as manufactured are cut, as shown in FIG. 5, to alter their configuration, which changes the spring rate of the leaf spring, while material can be added to the springs to increase the spring rate. In the embodiment shown, cut 110 reduces the spring width, as shown at 100, the cut being centered generally at a point equidistant between the two ends 102, 104 of the spring element 106, to minimize fatigue-generating stresses. The depth of the cut (across the width of the spring) is selected to produce the degree of tuning required. The variables of the cut include the overall length of the cut, the configuration, i.e. the curvature of the cut, and the width of the cut. In the specific embodiment shown, the cut 110 is curved in configuration. It should be understood, however, that other cut configurations can be used. One alternative is a "football" shaped slot in the center of one or both springs. Variables for this cut include the location of the slot, the length and/or width of the slot and the curvature of the slot. The cut can be accomplished by a number of techniques, including a laser, a grinder or a conventional cutting tool. The manner in which the material is removed is not significant to the invention.

After the cut has been made, another test is made to confirm that the frequency of the structure is within accepted tolerance. If not, additional cuts can be made to bring the device into tolerance. The result of the tuning of the present system is that the manufacturing tolerance of such appliances need no longer be as severe as heretofore. This will reduce the number of rejects of the manufactured product. In addition, the tuning can be accomplished quickly and efficiently during manufacturing and the appliance requires no additional tuning thereafter.

Hence, first, a new motion conversion assembly from side-by-side to rotary action for an appliance such as a toothbrush has been disclosed, using in one preferred embodiment leaf springs which are configured to be less resistant to twisting than to bending, even though there is some bending by the spring assembly, in addition to the twisting, to produce the desired rotary action of a drive shaft on which the workpiece is mounted. High resistance to bending eliminates the need for bearings. The motion being converted is referred to as side-to-side, which includes a straight line movement as well as movement which includes a slight arc, as in the present embodiment. The workpiece motion is rotary, about the axis of the drive shaft on which the workpiece is mounted. Second, a method has been disclosed for tuning a spring assembly system to change the resonant frequency of the system during manufacturing to conform to the desired operating frequency (driving frequency) of the system. This permits the use of less severe manufacturing tolerances.

Although a preferred embodiment of both the motion conversion system and method of tuning has been described for purposes of illustration, it should be understood that various changes, modification and substitutions can be used in such embodiments without departing from the spirit of the invention which is defined by the claims which follow.

What is claimed:

1. An apparatus for converting side-to-side substantially linear drive motion to rotational motion for a workpiece portion of an appliance, comprising:

a movable base mounting element, capable of being driven in a side-to-side substantially linear reciprocal motion;

a fixed position mounting element spaced apart from the base element, wherein the fixed mounting element is held in position so that it does not move during operation of the apparatus;

a spring member connected to the movable base element and fixedly connected to the fixed mounting element; and a drive shaft member connected to the base element and rotatable relative to the fixed mounting element, the drive shaft having a workpiece mounted thereto;

wherein the spring member is so configured and arranged that it is substantially less resistant to twisting action than to bending action, the twisting action producing workpiece rotation at a preselected frequency.

2. An apparatus of claim 1, wherein the spring member comprises two separate, flat planar springs.

3. An apparatus of claim 1, wherein the spring member is a single planar spring.

4. An apparatus of claim 1, wherein the spring member is two orthogonal wire form springs.

5. An apparatus of claim 1, wherein the spring member comprises a plurality of planar spring members spaced at regular intervals between the base mounting element and the fixed mounting element.

6. An apparatus of claim 1, wherein the side-to-side motion of the base mounting element is accomplished by a magnetic driver arrangement which includes permanent magnets positioned on the movable base mounting element and an electromagnetic driver spaced apart from the permanent magnets in a base portion of the appliance.

7. An apparatus of claim 1, wherein the appliance is a toothbrush.

8. An apparatus of claim 1, wherein the appliance is a shaver.

9. An apparatus of claim 2, wherein the two planar springs are separated by a selected angle along the length thereof.

10. An apparatus of claim 9, wherein the angle is approximately 90°±40°.

11. An apparatus of claim 9, wherein the drive shaft member is located at an intersection of the respective planes of the two springs.

12. An apparatus of claim 1, wherein the drive shaft member extends for a distance beyond the fixed mounting element and wherein the workpiece is a brushhead.

13. An apparatus of claim 1, wherein the spring member and the drive shaft member are both metal.

14. An apparatus of claim 1, wherein the drive shaft member and the spring member are both positioned at a selected angle away from the longitudinal axis of the appliance.

15. An apparatus of claim 1, including a positioning member which maintains the fixed mounting element from moving during operation of the appliance, and wherein the positioning member includes extending portions which mate with receiving portions in a handle portion of the appliance, preventing the positioning assembly from rotating.

16. An apparatus of claim 14, wherein the selected angle is within the range of 5–15°.

17. An apparatus of claim 1, wherein the drive shaft member extends from the movable base element in one direction approximately to the fixed mounting element and in the opposing direction to the rear of the base element a selected distance, wherein the workpiece extends for substantially the length of the drive shaft member.

18. An appliance which includes a workpiece mounted on a drive shaft, comprising:
 a handle portion which houses a drive system for the appliance;
 an assembly for converting side-to-side substantially linear drive action of the drive system to rotational motion for the workpiece, which includes a movable base mounting element which is driven by the drive system in a side-to-side substantially linear reciprocal motion;
 a fixed mounting element spaced apart from the base element, wherein the fixed mounting element is held in position so that it does not move during operation of the apparatus;
 a spring member connected to the movable base element and fixedly connected to the fixed mounting element;
 a drive shaft member connected to the base element and rotatable relative to the fixed mounting element; and
 a workpiece attached to the drive shaft member, wherein the spring member is so configured that it is substantially less resistant to twisting action than to bending action, the twisting action producing workpiece rotation at a preselected frequency.

19. An apparatus of claim 18, wherein the spring member comprises two separate, flat planar springs.

20. An apparatus of claim 18, wherein the spring member is a single planar spring.

21. An apparatus of claim 18, wherein the side-to-side motion of the movable base mounting element is accomplished by a magnetic driver arrangement comprising permanent magnets positioned on the movable base element and an electromagnetic driver spaced apart from the permanent magnets in a handle portion of the appliance.

22. An apparatus of claim 18, wherein the appliance is a toothbrush.

23. An apparatus of claim 19, wherein the two planar springs are separated by a selected angle along the length thereof.

24. An apparatus of claim 18, wherein the drive shaft member and the spring member are both positioned at a selected angle away from the longitudinal axis of the appliance.

25. An apparatus of claim 18, wherein the drive shaft element extends from the movable base element in one direction approximately to the fixed mounting element and in the other direction to the rear of the base element a selected distance, wherein the workpiece extends for substantially the length of the drive shaft member, and wherein the appliance is a shaver.

26. An apparatus of claim 18, including a positioning member which maintains the fixed mounting element from moving during operation of the appliance, and wherein the positioning member includes extending portions which mate with receiving portions in the handle portion of the appliance, and further including a cover element, wherein one end of the cover element is threadably connected to the handle and the other end mates with a proximal end of a housing for the drive shaft member and wherein the positioning member is mounted to an inside surface of the cover element.

27. An apparatus for converting side-to-side substantially linear drive motion to rotational motion for a workpiece portion of an appliance, comprising:
 a movable base mounting element, capable of being driven in a side-to-side substantially linear reciprocal motion;
 a fixed position mounting element, wherein the fixed mounting element is held in position so that it does not move during operation of the apparatus;
 a spring assembly connected to the movable base element and fixedly connected to the fixed mounting element; and
 a drive shaft member connected to the base element and extending away from the movable base element and the fixed mounting element, the drive shaft having a workpiece connected thereto;
 wherein the spring member is so configured and arranged that it is substantially less resistant to twisting action than to bending action, the twisting action producing workpiece rotation at a preselected frequency.

* * * * *